(12) United States Patent
Winegar et al.

(10) Patent No.: US 12,256,898 B2
(45) Date of Patent: Mar. 25, 2025

(54) INTRODUCER SHEATHS FOR ENDOSCOPES AND RELATED METHODS

(71) Applicant: CooperSurgical, Inc., Trumbull, CT (US)

(72) Inventors: Thomas William Winegar, Trumbull, CT (US); Rosemary Michelle Garofalo, North Haven, CT (US)

(73) Assignee: CooperSurgical, Inc., Trumbull, CT (US)

( * ) Notice: Subject to any disclaimer, the term of this patent is extended or adjusted under 35 U.S.C. 154(b) by 750 days.

(21) Appl. No.: 17/484,222

(22) Filed: Sep. 24, 2021

(65) Prior Publication Data

US 2022/0079620 A1     Mar. 17, 2022

Related U.S. Application Data

(63) Continuation of application No. 15/451,583, filed on Mar. 7, 2017, now abandoned.
(Continued)

(51) Int. Cl.
    *A61B 1/00*         (2006.01)
    *A61B 1/303*       (2006.01)
    (Continued)

(52) U.S. Cl.
    CPC ...... *A61B 1/00154* (2013.01); *A61B 1/00085* (2013.01); *A61B 1/00135* (2013.01);
    (Continued)

(58) Field of Classification Search
CPC .. A61B 1/00135; A61B 1/00154; A61B 1/032
See application file for complete search history.

(56) References Cited

U.S. PATENT DOCUMENTS

| 1,856,295 A | 5/1932 | Sovatkin |
| 2,186,143 A | 1/1940 | Neugass |

(Continued)

FOREIGN PATENT DOCUMENTS

| DE | 201 10 921 | 12/2001 |
| DE | 695 32 474 | 11/2004 |

(Continued)

OTHER PUBLICATIONS

Culligan et al., "Long-Term Success of Abdominal Sacral Colpopexy Using Synthetic Mesh," Am. J. Obstet. Gynecol., Dec. 2002.
(Continued)

*Primary Examiner* — Aaron B Fairchild
(74) *Attorney, Agent, or Firm* — Fish & Richardson P.C.

(57) ABSTRACT

A sheath for inserting a cannula of an endoscope into a cavity of a patient is described herein. The sheath comprises an introducer, a support channel and a pull-tab. The introducer has an open end being sized and shaped to accept a tip of the cannula and a tip end adapted to be deflected in an outward direction by the tip of the cannula passing into the introducer. The support channel is adapted to receive a shaft of the cannula and guide the tip of the cannula into the introducer; and the pull provides a finger hold for a user to grasp the sheath. In some aspects, the introducer includes a plurality of extending segments having a normally closed position defining a conical exterior shape of the introducer, with the plurality of tapered segments adapted to be separated by the tip of the cannula passing through the introducer.

16 Claims, 12 Drawing Sheets

Related U.S. Application Data (60) Provisional application No. 62/309,121, filed on Mar. 16, 2016.

(51) Int. Cl.
  *A61B 1/32* (2006.01)
  *A61B 17/34* (2006.01)
  *A61B 17/42* (2006.01)
  *A61M 25/06* (2006.01)
  *A61B 17/02* (2006.01)

(52) U.S. Cl.
  CPC .............. *A61B 1/303* (2013.01); *A61B 1/32* (2013.01); *A61B 17/3415* (2013.01); *A61B 17/3421* (2013.01); *A61B 17/3439* (2013.01); *A61B 17/4241* (2013.01); *A61M 25/0668* (2013.01); *A61B 17/0218* (2013.01); *A61B 2017/345* (2013.01); *A61B 2017/3454* (2013.01); *A61M 2025/0687* (2013.01)

(56) References Cited

U.S. PATENT DOCUMENTS

| | | |
|---|---|---|
| 2,456,806 A | 12/1948 | Wolffe |
| 2,744,708 A | 5/1956 | Bedford, Jr. |
| 3,096,764 A | 7/1963 | Hiebert |
| 3,131,690 A | 5/1964 | Innis et al. |
| 3,153,267 A | 10/1964 | Rowland, Jr. |
| 3,196,865 A | 7/1965 | Rose |
| 3,749,088 A | 7/1973 | Kohlmann |
| 3,766,909 A | 10/1973 | Ozbey |
| 3,769,983 A | 11/1973 | Merav |
| 3,877,429 A | 4/1975 | Rasumoff |
| 3,877,433 A | 4/1975 | Librach |
| 3,878,848 A | 4/1975 | Hiebert |
| 3,948,270 A | 4/1976 | Hasson |
| 4,022,208 A | 5/1977 | Valtchev |
| 4,066,071 A | 1/1978 | Nagel |
| 4,323,057 A | 4/1982 | Jamieson |
| 4,430,076 A | 2/1984 | Harris |
| 4,533,349 A | 8/1985 | Bark |
| 4,562,832 A | 1/1986 | Wilder et al. |
| 4,597,030 A | 6/1986 | Brody et al. |
| 4,627,421 A | 12/1986 | Symbas et al. |
| 4,775,362 A | 10/1988 | Kronner |
| 4,807,625 A | 2/1989 | Singleton |
| 4,823,167 A | 4/1989 | Manska et al. |
| 4,981,355 A | 1/1991 | Higgins |
| 4,996,974 A | 3/1991 | Ciarlei |
| 4,997,419 A | 3/1991 | Lakatos et al. |
| 5,059,198 A | 10/1991 | Gimpelson |
| 5,104,377 A | 4/1992 | Levine |
| 5,174,276 A | 12/1992 | Crockard |
| 5,181,842 A | 1/1993 | Sunderland et al. |
| 5,209,754 A | 5/1993 | Ahluwalia |
| 5,232,443 A | 8/1993 | Leach |
| 5,237,985 A | 8/1993 | Hodgson et al. |
| 5,242,240 A | 9/1993 | Gorham |
| 5,259,836 A | 11/1993 | Thurmond et al. |
| 5,273,026 A | 12/1993 | Wilk |
| 5,338,297 A | 8/1994 | Kocur et al. |
| 5,353,784 A | 10/1994 | Nady-Mohamed |
| 5,409,496 A | 4/1995 | Rowden et al. |
| 5,431,662 A * | 7/1995 | Nicholas ............ A61B 17/0218 606/119 |
| 5,520,698 A | 5/1996 | Koh |
| 5,540,700 A | 7/1996 | Rowden et al. |
| 5,549,563 A | 8/1996 | Kronner |
| 5,571,115 A | 11/1996 | Nicholas |
| 5,624,399 A | 4/1997 | Ackerman |
| 5,643,285 A | 7/1997 | Rowden et al. |
| 5,690,617 A | 11/1997 | Wright |
| 5,810,806 A | 9/1998 | Ritchart et al. |
| 5,835,657 A | 11/1998 | Suarez et al. |
| 5,840,077 A | 11/1998 | Rowden et al. |
| 6,068,121 A | 5/2000 | McGlinch |
| 6,080,118 A | 6/2000 | Blythe |
| 6,159,170 A | 12/2000 | Borodulin et al. |
| 6,328,729 B1 | 12/2001 | Jervis |
| 6,348,036 B1 | 2/2002 | Looney et al. |
| 6,423,075 B1 | 7/2002 | Singh et al. |
| 6,447,444 B1 | 9/2002 | Avni et al. |
| 6,569,085 B2 | 5/2003 | Kortenbach et al. |
| 6,651,992 B1 | 11/2003 | Smith, Sr. |
| 6,682,100 B2 | 1/2004 | Wood et al. |
| 6,741,895 B1 | 5/2004 | Gafni et al. |
| 6,752,819 B1 | 6/2004 | Brady et al. |
| 6,932,759 B2 | 8/2005 | Kammerer et al. |
| 7,052,453 B2 | 5/2006 | Presthus et al. |
| 7,334,503 B1 | 2/2008 | Newman |
| 8,579,800 B2 | 11/2013 | Emura et al. |
| 8,939,988 B2 | 1/2015 | Auerbach et al. |
| 2001/0021854 A1 | 9/2001 | Donnez et al. |
| 2002/0026195 A1 | 2/2002 | Layne et al. |
| 2003/0187334 A1 | 10/2003 | Biswas |
| 2003/0195386 A1 | 10/2003 | Thierfeld et al. |
| 2003/0220538 A1 | 11/2003 | Jacquetin |
| 2004/0138528 A1 | 7/2004 | Richter et al. |
| 2004/0193043 A1 | 9/2004 | Duchon et al. |
| 2004/0230092 A1 | 11/2004 | Thierfeld et al. |
| 2005/0065395 A1 | 3/2005 | Mellier |
| 2005/0085827 A1 | 4/2005 | G et al. |
| 2005/0090852 A1 | 4/2005 | Layne et al. |
| 2005/0107818 A1 | 5/2005 | Valtchev |
| 2005/0277948 A1 | 12/2005 | Cedars |
| 2006/0015001 A1 | 1/2006 | Staskin et al. |
| 2006/0199994 A1 | 9/2006 | Inman et al. |
| 2006/0241652 A1 | 10/2006 | Doll et al. |
| 2007/0088351 A1 | 4/2007 | Ewaschuk et al. |
| 2007/0129615 A1 | 6/2007 | Backman et al. |
| 2008/0221590 A1 | 9/2008 | Ikeda et al. |
| 2008/0243176 A1 | 10/2008 | Weitzner et al. |
| 2008/0249534 A1 * | 10/2008 | Gruber ............... A61M 31/002 606/198 |
| 2008/0249535 A1 | 10/2008 | Valtchev |
| 2009/0131954 A1 | 5/2009 | Christian et al. |
| 2010/0106163 A1 | 4/2010 | Blair et al. |
| 2010/0152749 A1 | 6/2010 | Von Pechmann et al. |
| 2010/0168784 A1 | 7/2010 | Pustilnik |
| 2010/0179575 A1 | 7/2010 | Von Pechmann et al. |
| 2010/0280309 A1 | 11/2010 | Von Pechmann |
| 2010/0305578 A1 | 12/2010 | Auerbach et al. |
| 2011/0130769 A1 | 6/2011 | Boebel et al. |
| 2012/0083740 A1 | 4/2012 | Chebator et al. |
| 2013/0225934 A1 | 8/2013 | Raybin et al. |
| 2015/0238684 A1 | 8/2015 | Dai et al. |
| 2016/0038133 A1 | 2/2016 | Smith et al. |
| 2016/0192828 A1 | 7/2016 | Sexton |
| 2016/0270816 A1 | 9/2016 | Mather et al. |
| 2017/0265892 A1 | 3/2017 | Winegar et al. |

FOREIGN PATENT DOCUMENTS

| | | |
|---|---|---|
| DE | 103 41 561 | 4/2005 |
| EP | 0 400 458 | 12/1990 |
| EP | 0 890 342 | 9/2003 |
| WO | WO 2008/074054 | 6/2008 |
| WO | WO 2009/078953 | 6/2009 |

OTHER PUBLICATIONS

"KOH Cup Vaginal Fornices Delineator & Colpo-Pneumo Occluder," *The Koh Colpotomizer™ System*, Directions for Use; 6 pages; Sep. 2008.

"Laparoscopic Hysterectomy and Colpotomy Accessories for Use Exclusively with the RUMI System Uterine Manipulator," *CooperSurgical The KOH Colpotomizer System*; 2 pages; Oct. 2006.

* cited by examiner

FIG. 9

# INTRODUCER SHEATHS FOR ENDOSCOPES AND RELATED METHODS

CROSS-REFERENCE TO RELATED APPLICATION

This application is a continuation of and claims priority under 35 U.S.C. § 120 from U.S. application Ser. No. 15/451,583, filed on Mar. 7, 2017, which claims priority to U.S. Provisional Patent Application No. 62/309,121, filed on Mar. 16, 2016. The entire contents of each of these priority applications are incorporated herein by reference.

FIELD

The present invention relates to a sheath for aiding insertion of an endoscope, such as a hysteroscope, cystoscope, ureteroscope, or laparoscope into a cavity, such as a uterus, urinary bladder, ureters or abdominal cavity of a patient.

BACKGROUND

Hysteroscopy, or direct vision of the inside of the uterus, has been shown to improve diagnostic accuracy. However, patients often find the insertion and removal of the hysteroscopy apparatus and, subsequently, the endoscopic apparatus into the patient's uterine cavity uncomfortable. Typical hysteroscopy devices have a distal tip end sized to facilitate insertion of the tip end through the patient's cervix and into the uterus.

SUMMARY

Certain aspects of the invention relate to a sheath for inserting a cannula of a hysteroscope through a cervix and into the uterus of a patient. The present invention can also relate to passing tools, such as an endoscope, laparoscope, or others into an anatomical space. The present invention further relates to passing tools when such passage may otherwise be difficult, such as into a urinary bladder through a constriction such as structure or sphincter. The sheath includes an introducer positioned at a distal end of the sheath. The introducer has a tip end and an open end at a distal end of the introducer. The open end is sized and shaped to accept a tip of the cannula. The sheath includes a support channel adapted to receive a shaft of the cannula and guide the tip of the cannula into the introducer.

In some examples, the introducer is biased in a normally closed position.

In some examples, the introducer is biased in a normally deflected-open position, and the tip end adapted to be defected inwardly prior to insertion of the sheath.

In some examples, the tip end is adapted to be deflected in the outward direction by the tip of the cannula when the tip of the cannula is inserted into the introducer.

In some examples, the support member includes an outer sleeve and an inner sleeve, the inner sleeve being slidably disposed in the outer sleeve, and the tip end of the introducer is adapted to be deflected in the outward direction by the inner sleeve when a distal end of the inner sleeve is inserted into the introducer.

In some examples, a pull-tab extending from a proximal end of the sheath provides a finger hold for a user to grasp the sheath.

In some examples, the support channel includes a retention clasp adapted to removeably secure the shaft of the cannula to the support channel.

In some examples, the sheath is constructed from a lubricious material or coated in a lubricious material.

In some examples, the sheath has an overall length of 127 mm to 304.8 mm.

In some examples, the introducer has a length of 15 mm to 70 mm (e.g., about 30 mm). In some examples, introducer has an exterior diameter of 2 mm to 30 mm (e.g., about 7.8 mm).

In some examples, the introducer defines a tapered or conical exterior surface.

In some examples, the introducer includes a ring at the open end, and a plurality of segments that extend from the ring to the tip end. The plurality of tapered segments have a normally closed position that define a conical exterior shape of the introducer, and the plurality of tapered segments are adapted to be separated in a radial direction by the tip of the cannula passing through the introducer. When separated, the segments enable the cannula to pass through the introducer.

In some examples, the introducer includes a ring at the open end, and a plurality of segments that extend from the ring to the tip end. The pluralities of tapered segments have a normally open position. The segments forming a conical exterior shape of the introducer are adapted to be closed by a user prior to insertion, and the plurality of tapered segments are adapted to be separated in a radial direction based on material properties. When separated, the segments enable the cannula to pass through the introducer.

In some examples, the conical exterior shape is formed as a single tapered segment. The radial expansion of the single tapered segment is enabled by material property such as the elasticity or an elastomer.

In some examples, each of the plurality of tapered segments defines a triangular shape. In some examples, the plurality of tapered segments together define a frustoconical shape.

In some examples, each of the plurality of tapered segments defines outsides edges that are positioned adjacent to the outside edge of an adjacent tapered segment in the normally closed position, and the outsides edges of each of the plurality of tapered segments are adapted to be separated by the tip of the cannula passing through the introducer.

In some examples, the support member includes one or more depth markings located on the support channel to identify how far the cannula tip has been inserted into an internal space.

In some examples, the introducer includes a coiled segment extending from the support tube to the tip end in an overlapping spiral. The coiled segment has a normally tapered portion defining a conical exterior shape of the introducer. In some examples, the normal position derives a cylindrical exterior shape of the introducer. The tip end of the introducer accepts the tip of the cannula, and the coiled segment is adapted to at least partially uncoil when the cannula shaft is translated toward the tip end. In some examples, the uncoiling is caused directly by the translation of the cannula which increases the diameter of the introducer at the tip end. The increasing diameter enables the cannula to pass through the introducer.

Another example is a method of inserting a cannula of a hysteroscope through a cervix and into the uterus of a patient using a sheath. The method includes placing a cannula within a support channel of the sheath, proximal to a collapsed introducer at the insertion end of the sheath, and advancing the cannula and sheath through a vaginal canal until the collapsed introducer is inserted into a cervical canal. The introducer at least partially dilates the cervical canal. The cannula is advanced along the support channel and through the introducer. The advancing cannula expands the introducer and further dilates the cervical canal. The cannula is advanced within the support channel to a desired distance within the uterine cavity. The cannula and sheath are then removed from the patient.

In some examples, advancing the cannula through the introducer expands the introducer and further dilates the internal space.

In some examples, the method further includes advancing an inner sheath of the cannula along the support channel and into the introducer, the advancing of the inner sheath expanding the introducer and further dilating the internal space to enable the advancing of the cannula though the introducer and into the cavity.

In some examples, the method further includes, when the distal end of cannula reaches a desired location, securing the proximal end of cannula within the retention clasps of the sheath.

In some examples, the method further includes advancing the cannula and sheath until a pull-tab of the sheath contacts the patient anatomy or vaginal opening/introitus of the patient.

In some examples, the method further includes orienting the cannula in a desired position, guided by feedback from the stiffness of the introducer.

In some examples, orienting the cannula in a desired position is enabled by the introducer adding stiffness to the cannula.

In some examples, the method further includes performing diagnostic procedures in the uterine cavity with the distal end of the cannula. In some examples, the diagnostic procedures include acquiring images of the uterine cavity with the distal end of the cannula.

In some examples, removing the cannula and sheath from the patient includes removing the cannula and sheath together, at the same time, from the cervix by pulling on the cannula and a pull-tab on the proximal end of the sheath. In other examples, removal of the cannula and the sheath together is enabled through a reversible attachment between the cannula and sheath. In other examples, the reversible attachment aligns the cannula in the sheath.

In some examples, removing the cannula and sheath from the patient includes removing the sheath from the patient while the cannula is still inserted within the cervix or uterine cavity.

Yet another example is a method of inserting a cannula of a hysteroscope through the cervix and into the uterus of a patient using a coiled sheath. The method comprises mounting the coiled sheath on a distal end of the cannula, and advancing the cannula and coiled sheath through a vaginal canal until a distal end of the coiled sheath is inserted into a cervical canal. The distal end of the coiled sheath partially dilates the cervical canal. The method also includes advancing the cannula through the coiled sheath to a desired distance within the uterine cavity. The advancing cannula radially expands the coiled sheath and dilates the cervix.

In some examples, the method further includes orienting the cannula in a desired position, which is enabled by the stiffness of the coiled sheath.

In some examples, the method further includes removing the cannula and coiled sheath from the patient includes unwinding the coiled sheath from the cannula.

A sheath for inserting a cannula of a hysteroscope through a cervix and into the uterus of a patient is described herein.

The sheath includes an introducer to be inserted into a cervix and subsequently pass a tip of the cannula through the introducer, whereby the cannula deflects a portion of the introducer in an outward direction, to aid in the introduction of the tip of the cannula to the uterus. In some aspects, the introducer includes a plurality of extending segments having a normally closed position defining a conical exterior shape of the introducer, with the plurality of tapered segments adapted to be separated by the tip of the cannula passing through the introducer.

Embodiments can include one or more of the following advantages. In some embodiments, the sheath allows for easier insertion of a hysteroscope through the cervix and into a uterus of a patient. The sheath can allow for less painful hysteroscopy procedures because the distal end of the sheath has a smaller profile than the tip of the hysteroscope and, therefore, passes into the cervix more easily than the hysteroscope alone would. In certain embodiments, the sheath provides better steerability/maneuverability of the hysteroscope during a hysteroscopy procedure because, for example, the sheath can increase the overall rigidity of the effective rigidity of the hysteroscope. In some embodiments, the sheath can be removed from the patient while leaving the hysteroscope in the uterus and/or cervix. This can increase the comfort of the patient during the hysteroscopy procedure.

Other aspects, features, and advantages will be apparent from the description, the drawings, and the claims.

DETAILED DESCRIPTION

The present disclosure presents methods and devices to allow ease of insertion for a cannula or other tool to cross through a tight orifice, such as a cervix, for a procedure such as hysteroscopy. Additionally, some of the devices discussed herein can be mated to a flexible cannula or some other tool to provide the cannula or tool with increased stiffness, which can improve the user's ability to pass the cannula or tool though a tight orifice or can improve the user's ability to move the cannula or tool laterally or rotationally during use.

The embodiments disclosed herein describe devices and methods that provides easier access for a tool through a small, undilated orifice. In some embodiments, the device is a single use, disposable, generally cylindrical shape with a small distal opening. The distal opening is of a size to fit through a small orifice, such as the cervix of a nulliparous woman. A tool, such as the diagnostic cannula of a hysteroscope, can be placed down the inner diameter of the device. Both the inner diameter and outer diameter of the device grow with the passage of the tool, effectively dilating the orifice. In certain embodiments, the device has a longitudinal slit or opening that allows removal of the device without the removal of the tool. The tool can be left in place within the cavity and the device can slide along the long axis of the tool to remove the device from the patient. Then the slit or opening enables the device to move away from the long axis of the tool thereby removing the device from the tool.

Some examples of the present design improve insertion of hysteroscopes and similar devices through a cervix and into the uterus by providing a sheath to be inserted into the cervix, with a tip end that expands and dilates the cervix as a cannula of a hysteroscope passes through the sheath and past the cervix. Some examples of the sheath include a distal tip end of a sheath shaft split so that the distal tip end of the sheath collapses to make the tip smaller for insertion. Once the sheath is in the uterus, an instrument is able to be inserted down the cannula shaft and causes the distal tip to widen for passage. In some embodiments, the sheath passes into the uterus with the cannula. In some embodiments, the sheath maintains the dilation of the cervix while the cannula passes into the uterus. The instrument could also add rigidity to the assembly for ease of maneuverability, and the entire assembly is capable of rotation.

Some examples of the present design use an outer sheath that is initially inserted into the cervix as a dilator for a nulliparous cervix. The distal end of the sheath is small and the distal end expands open as the cannula travels down the sheath. In some instances, the sheath is made out of a stiffer material to aid with steering of the cannula. In certain embodiments, the sheath can be removed from the patient without removing the cannula. In some instances, this is be accomplished through the use of a longitudinal slit, a clamshell or hinged design that allows the sheath to open, or by removing a section of the sheath as through the use of a finger-grip.

Figure 1:
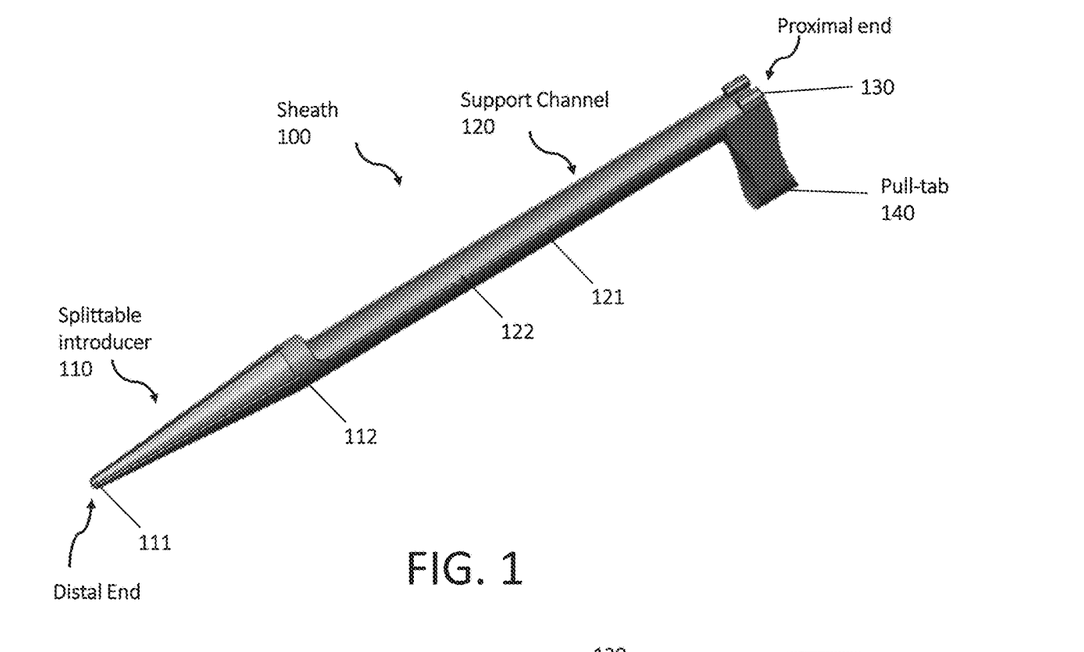
FIG. 1 is an illustration of a sheath with a splittable introducer in a normally closed position.

FIG. 1 is an illustration of a sheath 100 with a splittable introducer 110 in a normally closed position. As shown in FIG. 1 the splittable introducer 110 is provided at distal end of the sheath 100. A support channel 120 extends from the introducer 110 to a proximal end of the sheath 100. The support channel 120 includes a curved channel surface 122 formed into a rigid support member 121 and a pull-tab 140 secured to the rigid support member 121. The support channel 120 also includes a retention clasp 130 extending above the curved channel surface 122 at the proximal end of the sheath 100. The splittable introducer 110 includes a tip end 111 and a ring 112. The ring 112 forms an opening to the splittable introducer 110 and the ring 112 defines an inner surface that is joined with the curved channel surface 122 of the support channel 120.

The splittable introducer 110 includes segments that open or separate. Continuing to refer to FIG. 1, the splittable introducer 110 defines a conical exterior shape between the ring 112 and the tip end 111 to aid insertion of the splittable introducer 110 into an orifice. The pull-tab 140 is positioned at the proximal end of the sheath 100 to provide a finger-grip for manipulation of the sheath 100. For example, the pull-tab 140 may be used to withdraw the sheath 100 from an orifice after insertion. The pull grip 140 may be a grip region having a gripping surface, finger-holds, or a textured surface for increasing the friction between a user's fingers and the sheath 100. The retention clasp 130 is adapted to secure a cannula to the support channel 120 by providing, for example, a friction fit or deflection fit against the shaft of a cannula placed against curved channel surface 122.

In operation, the sheath 100 helps with insertion of a cannula into stenotic cervix, or into a tight cervix, which is sometimes the case for a nulliparous woman (a woman who has never given vaginal birth). Additionally, the rigid support member 121 increases the stiffness of the sheath 100 and, in some instances, aids in guiding the cannula through the cervix and into desired position within uterine cavity when the cannula is placed in the curved channel surface 122.

The sheath 100 may be constructed from a lubricious material, such as Teflon (PTFE), or plastics compounded with fluorinated oils. Alternatively, or additionally, a lubricious coating can be applied to the sheath. Examples of material from which the sheath can be formed include polypropylene, polycarbonate, or other common plastics. Examples of materials from which the lubricious coating can be formed include hydrogels, hydrophilic coatings, such as Baymedix, Parylene, and other surface modification technologies.

Figure 2:
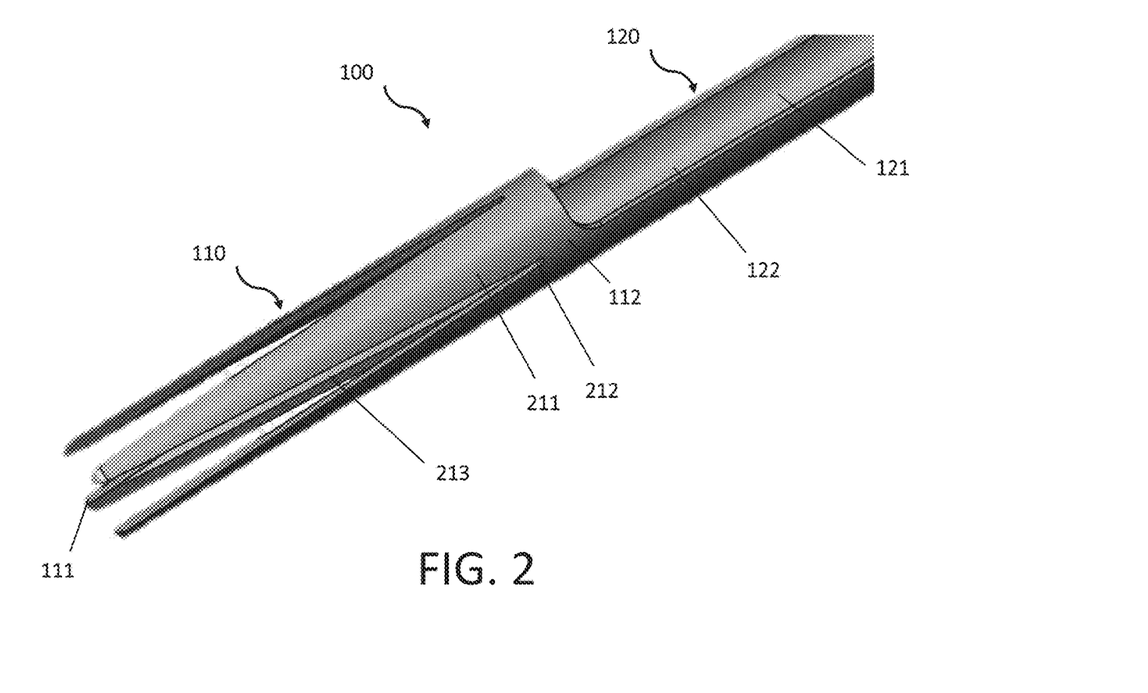
FIG. 2 is an illustration of the sheath of FIG. 1 with the splittable introducer in an open position.

FIG. 2 is an illustration of the sheath of FIG. 1 with the splittable introducer 110 in an open position. The splittable introducer 110 of the sheath 100 is formed from a plurality of conic segments 211 extending in a tapered triangular shape from the ring 112 to the tip end 111 of the splittable introducer 110. Each of the conic segments 211 forms a portion of the cone shape of the splittable introducer 110, and the plurality of conic segments 211 are normally in a closed positioned (as shown in FIG. 1) to maintain a small diameter at the tip end 111 during insertion. The plurality of conic segments 211 are formed by longitudinal cuts 212 in the splittable introducer, forming edges 213 that enable each conic segment 211 to be deflected away from the central axis of the splittable introducer 110, as shown in FIG. 2, by an object being pushed through the interior cavity of the splittable introducer 110.

Figure 3A:
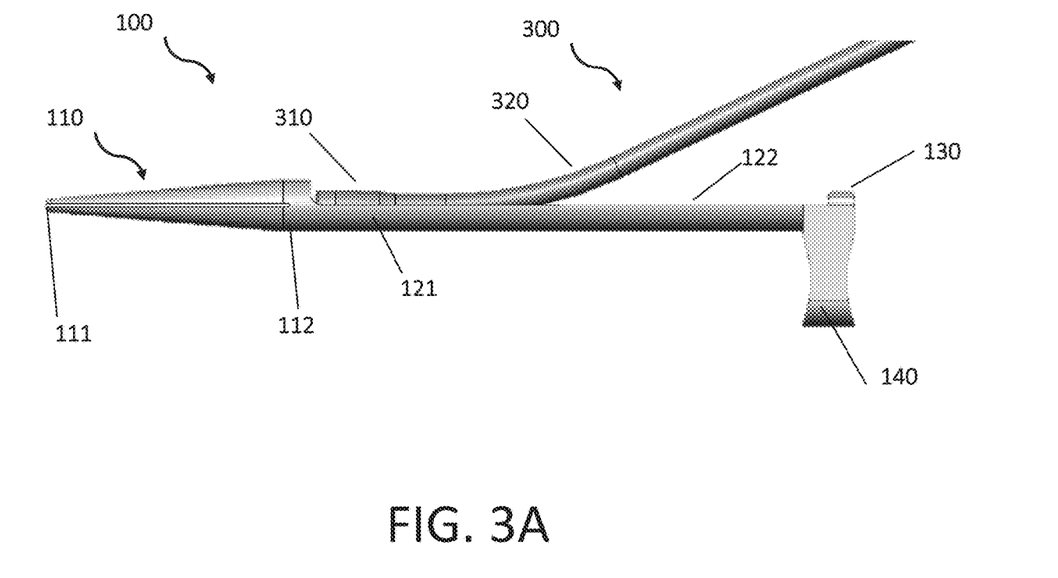
FIGS. 3A-3D are illustrations of a cannula being inserted into the sheath of FIG. 1.
Figure 3B:
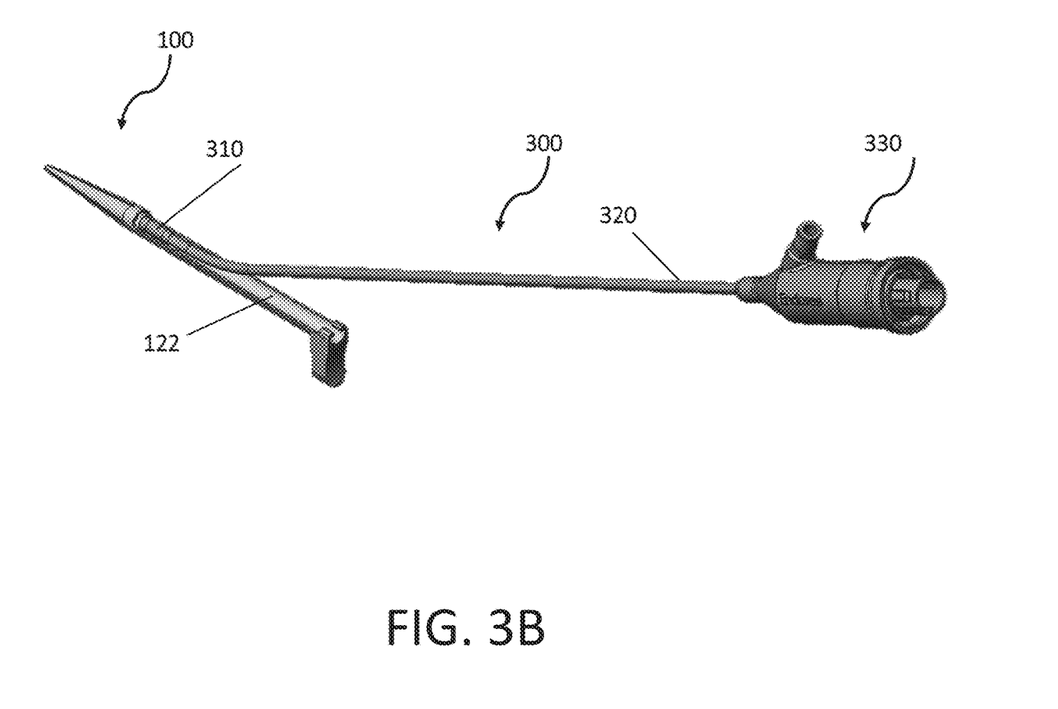

FIGS. 3A-3D are illustrations of a cannula 300 being inserted into the sheath 100 of FIG. 1. As shown in FIGS. 3A and 3B, the cannula 300 is placed on the curved support surface 122 of the sheath 100. The cannula 300 includes a proximal end connector 330, a shaft 320 and a distal tip 310. The distal tip 310 of the cannula is positioned adjacent to the ring 112 of the splittable introducer 110.

Figure 3C:
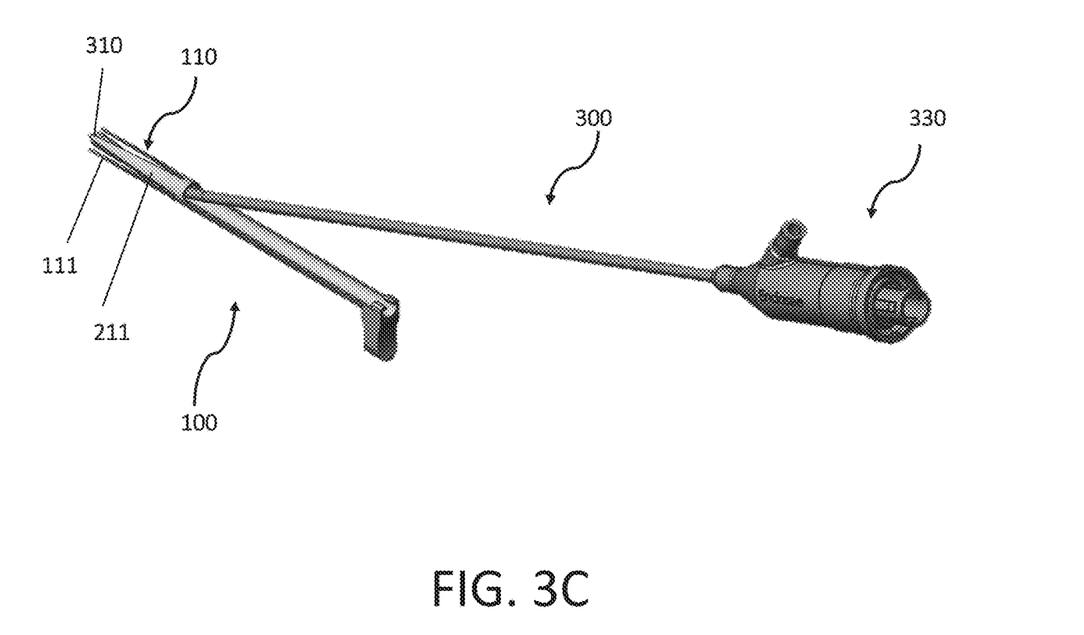

FIG. 3C shows the distal tip 310 of the cannula 300 inserted through the splittable introducer 110 of the sheath 100 until the distal tip 310 extends beyond the tip 310 of the splittable introducer. FIG. 3C shows the segments 211 of the introducer 110 are split by the distal tip 310. FIG. 3C shows the distal tip 310 and the shaft 320 of the cannula 300 pushed through the splittable introducer 110 until the proximal end of the sheath 100 is close to the proximal end of the cannula 300. The shaft 320 of the cannula 300 is secured to the sheath 100 by the retention clasp 130.

In an exemplary operation, the cannula 300 is placed within support channel 220 of the sheath 100, just proximal of splittable introducer 110, as shown in FIG. 3A, with tip end 111 of the splittable introducer 110 prepared to be inserted into a cervix of a patient. Next, the cannula 300 and sheath 100 are advanced through the vaginal canal until the collapsed splittable introducer 110 is inserted into a cervical canal (through most or all of cervical canal) of the patient, with the splittable introducer 110 helping to open the cervical canal as the increasing diameter of the splittable introducer 110 is introduced though the cervix. In some instances, the rigid support member 121 includes depth markings to indicate the length of the sheath 100 inserted into the patient. Next, the cannula 300 is advanced along the support channel 120 and through the splittable introducer 110 until the distal tip 310 of the cannula 300 is aligned with distal tip end 111 of the splittable introducer 110. This expands the splittable introducer 110 and thereby further dilates the cervical canal. This configuration is shown in more detail in FIG. 3E.

Figure 3D:
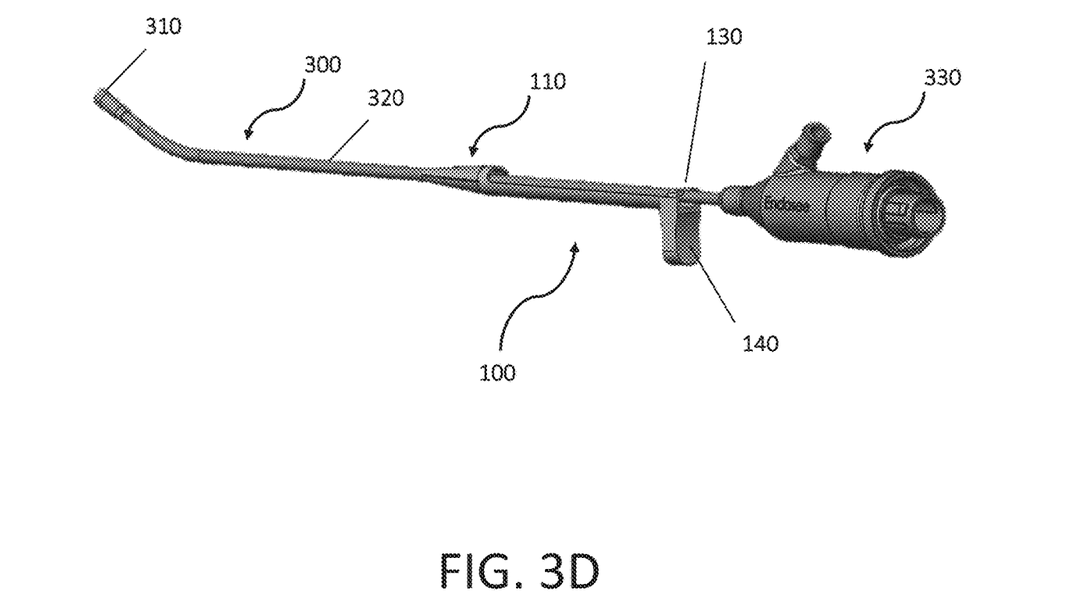

Once distal tip 310 of the cannula 300 reaches a desired depth, the proximal end of the shaft 320 of the cannula 300 is secured within the retention clasps 130 of the sheath 100. This helps to effectively increase the stiffness of the cannula, which, can be advantageous for positioning the cannula within the cavity. The cannula 300 can be further advanced within the support channel 120, as shown in FIG. 3D.

Once in position, the cannula 300 can be oriented or rotated to a desired position, as guided by the stiffness of the introducer. The increased stiffness acts to resist the force applied to the cannula by the cervix, allowing motion at the proximal end of the cannula to translate to the motion at the distal end, as opposed to motion at the proximal end causing the cannula to bend at the cervix rather than move the distal end. Diagnostic procedures can then be performed, for example, acquiring images of the uterine cavity with the distal tip 310 of the cannula 300, and finally the cannula 300 and sheath 100 are removed from the patient. The cannula 300 and sheath 100 can be removed together, at the same time, from the cervix by pulling on the cannula 300 and on the pull-tab 140 of the sheath 100, or the sheath 100 can be removed from the patient while the cannula 300 is still inserted within the cervix and/or uterine cavity (e.g., after advancement of the cannula to the desired position and before diagnostic procedures, or after diagnostic procedures) by pulling on pull-tab; then remove cannula.

Figure 3E:
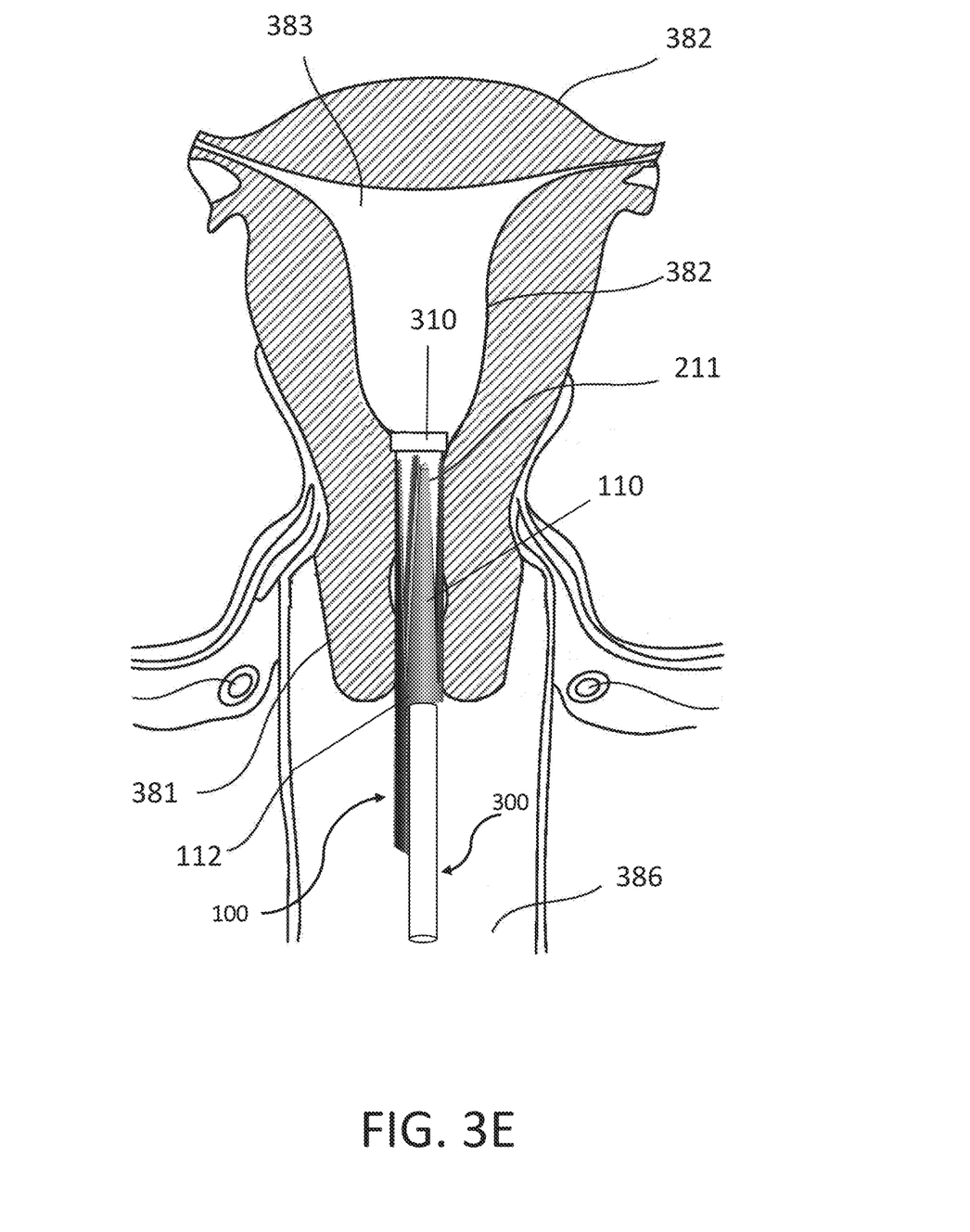
FIG. 3E is an illustration of the sheath of FIG. 1 aiding insertion of a cannula into the uterus of a patient.

FIG. 3E is an illustration of the sheath 100 of FIG. 1 aiding insertion of a cannula 300 into the uterus 382 of a patient. FIG. 3E shows sheath 100 present in the vaginal cavity 386 of a patient with the introducer 110 of the sheath 100 inserted into the cervix 381 of the patient. The distal tip 310 of the cannula 300 is shown passed through the introducer 110 and into the uterus 383 of the patient. The conic segments 211 of the introducer 110 are in a deflected position as a result of the distal tip 310 of the cannula passing through the introducer 110 and the deflection of the conic segments 211 is dilating the cervix 381 of the patient. In this configuration, the distal tip 310 of the cannula 300 is able to conduct typical procedures involving the uterus interior surface 383.

Figure 4A:
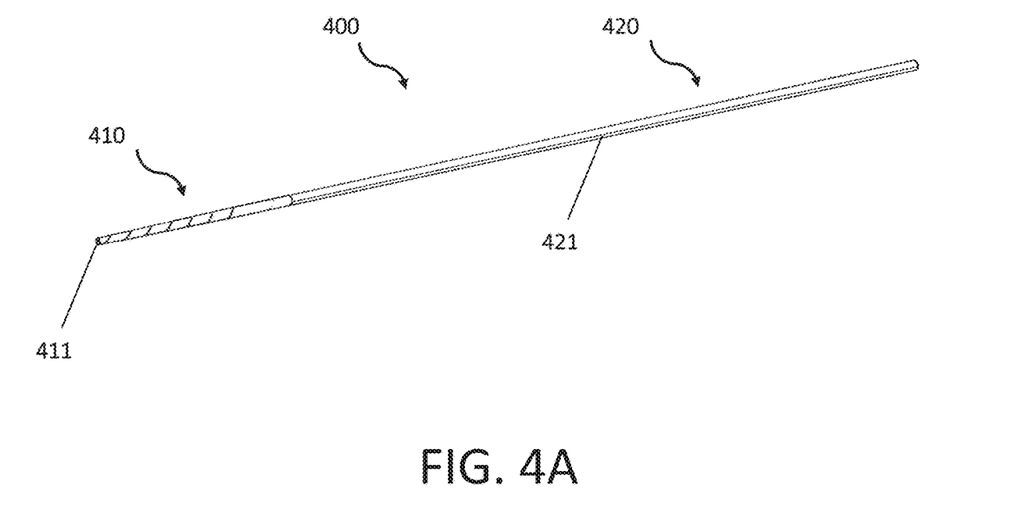
FIG. 4A is an illustration of a sheath with a coiled introducer in a normally coiled position.
Figure 4B:
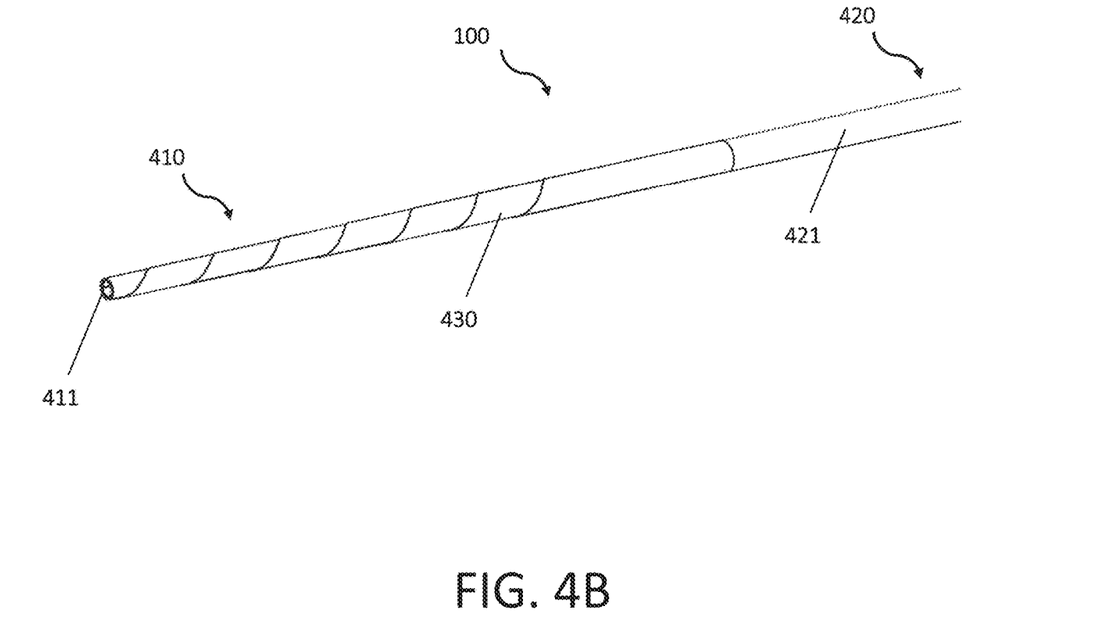
FIG. 4B is an enlarged view of a distal end region of the sheath of FIG. 4A.

While one embodiment has been discussed, many alternative designs and features exist. For example, FIGS. 4A and 4B are illustrations of a coiled sheath 400 with a coiled introducer 410 in a nominal position. As shown in FIG. 4A, the coiled sheath 400 forms a support shaft 420 and the introducer 410. The support shaft 420 defines a hollow tube 421 or curved surface 122 from the proximal end of the coiled sheath 400 to a distal tip end 411 of the introducer 410. The introducer 410 is detailed in FIG. 4B and defines a frustoconical shape in the nominal state.

The coiled sheath 400 may be a plastic sheath 430 that coils on itself. In its nominal state the introducer may have a length of 127 mm to 304.8 mm and an outer diameter of 0.5 mm to 30 mm. As a tool or other member passes through the ID of the introducer the coils unwind to dilate the cervix. Appropriate materials may include polypropylene, polystyrene, polycarbonate and other common medical device materials. In some instances, the tapered introducer 410 of the coiled sheath 400 is formed by maintaining the coiled sheath 400 in a helical shape and applying heat to remove stresses in the material and enable it to maintain the helical shape.

Figure 5A:
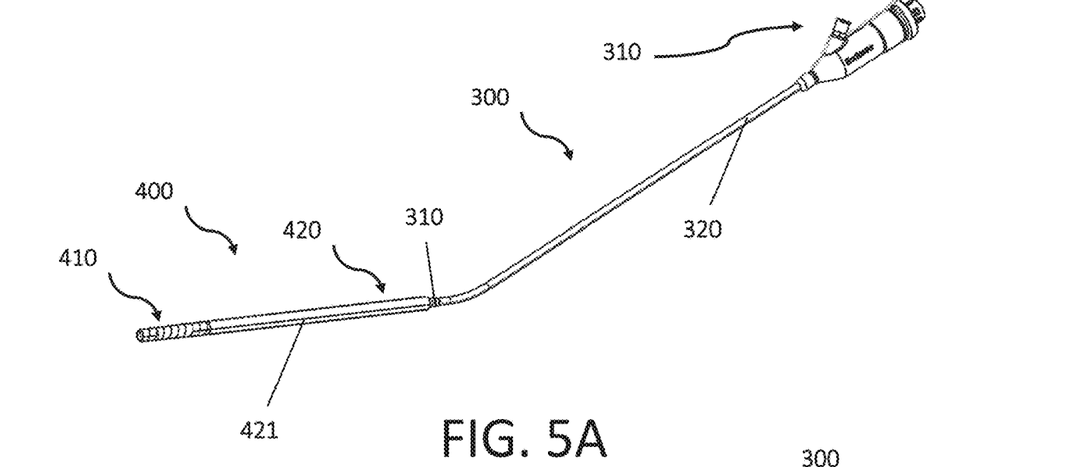
FIGS. 5A-5C are illustrations of a cannula being inserted into the sheath of FIG. 4A.
Figure 5B:
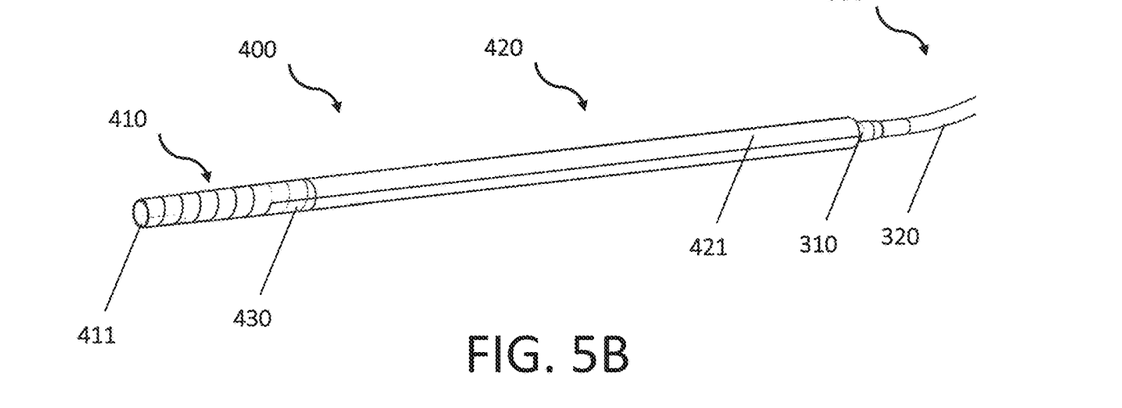
Figure 5C:
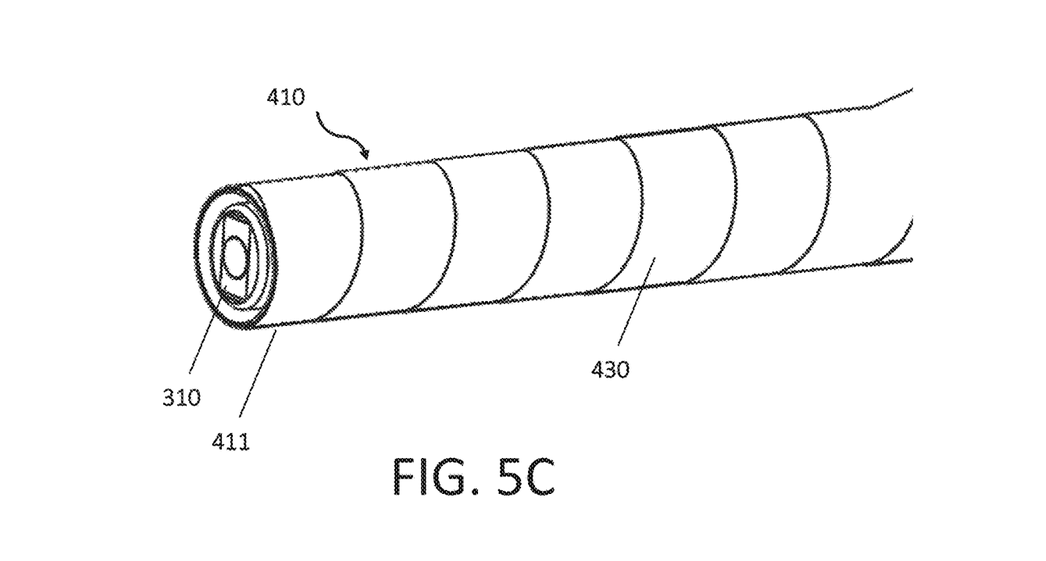

FIGS. 5A-5C are illustrations of a cannula 300 being inserted into the sheath of FIG. 4A. FIGS. 5A and 5B shows the distal tip 310 of the cannula 300 positioned to be inserted in the proximal end of the hollow tube 421 of the support shaft 420. FIG. 5C shows the distal tip 310 of the cannula 300 inserted through the coiled sheath 400 until it is located at the distal tip end 411 of the introducer 410. Passage of the cannula causes radial expansion of the introducer.

In operation, the coiled sheath 400 aids insertion of a cannula into stenotic cervix, or into a tight cervix, which is sometimes the case for a nulliparous woman. First, the coiled sheath 400 is mounted onto the distal end 310 of the cannula 300. Then, the cannula 300 and coiled sheath 400 are advanced through the vaginal canal of the patient until the distal tip end 411 of the elongated introducer 410 of the coiled sheath 400 is inserted into cervical canal (through all of cervical canal or just past distal end of cervical canal) of the patient. The introducer 410 helps to open the cervical canal. In some instances, the sheath 400 is introduced to the cervix prior to the introduction of the cannula 300 to the sheath 400. Next, the cannula 300 is advanced through the hollow tube 421 of the coiled sheath to a desired distance within uterine cavity, which causes the elongated introducer 410 to radially expands the coiled sheath 400, thereby dilating the cervix. Once in place, the cannula 300 can be oriented or rotated to a desired position, enabled by the stiffness of the coiled sheath, and diagnostic procedures can be performed, such as acquiring images of the uterine cavity with the distal end 310 of cannula 300. Finally, the cannula 300 and coiled sheath 400 are removed from the patient. In some instances, the cannula 300 and coiled sheath 400 are removed from the patient together. In some instances, the coiled sheath 400 is removed from the patient prior to the cannula. In this case, the coiled sheath 400 can be unwound to remove the coiled sheath 400 from the cannula.

While the coiled sheath 400 has been described as having a tapered introducer 410, in some instances the introducer 410 is cylindrical.

While the sheath 100 and 400 have been described as being used to facilitate the entrance of hysteroscopy into cavities, they could alternatively be used as introducers for facilitating the insertion of other medical devices, such as cardiac catheters, laparoscopes, and cystoscopes into small openings, such as strictures or sphincters. In some instances, the introducer 110 has a cylindrical shape. In some instances, the introducer 110 has a shape suitable for entry into a small opening and subsequently dilating the small opening by expanding the outer diameter of the introducer 110.

Figure 6A:
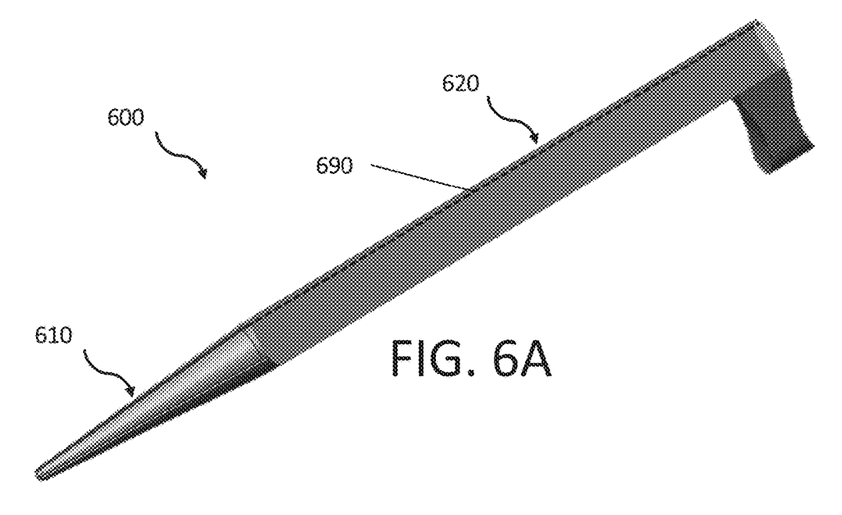
FIGS. 6A and 6B are illustrations of a sheath including a perforated body.
Figure 6B:
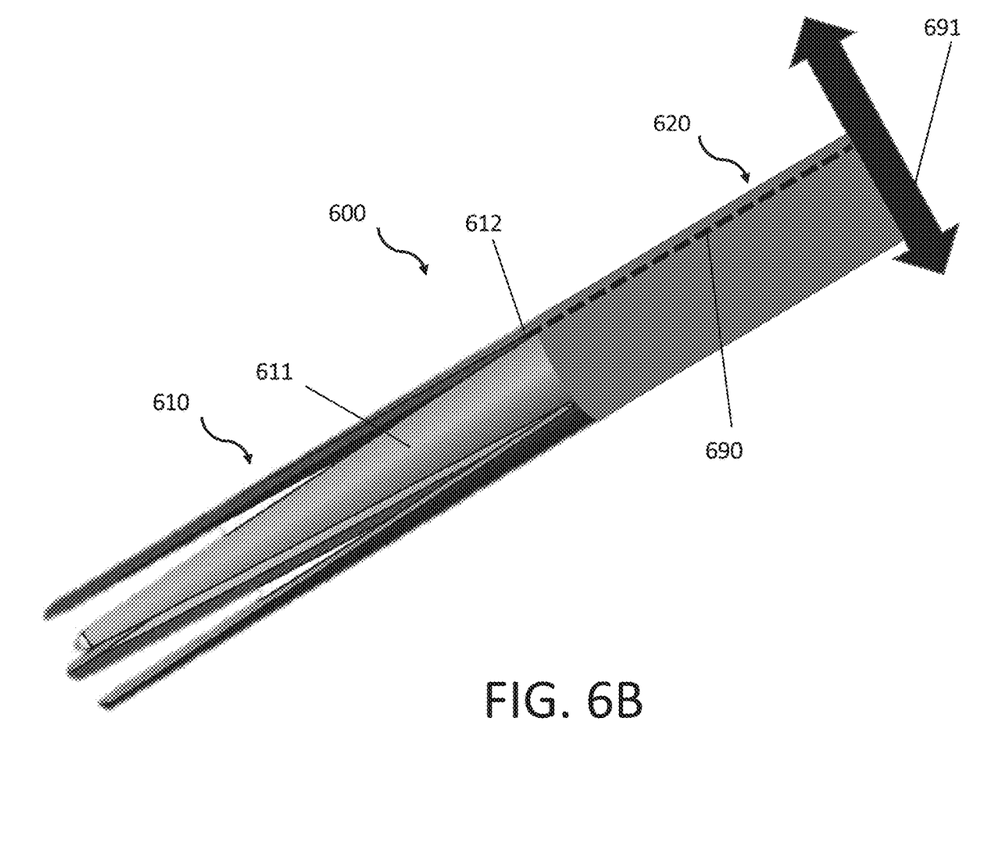

While the sheath 100 has been described as being removed from the patient while the cannula 300 is still inserted within the cervix 381 and/or uterine cavity 383 by translating the sheath 100 along the cannula 300, other features that allow the introducer 110 to be separated from the cannula 300 and removed from the patient separately from the cannula 300 can alternatively or additionally be used. In some embodiments, for example, the sheath is provided with a perforated slit that extends along the length of the sheath. While the sheath 100 has been described as having a support channel 120, in some embodiments the sheath 100 includes a tubular body adapted to accept the cannula 300. FIGS. 6A and 6B are illustrations of a sheath 600 including a perforated support tube 620 (including longitudinal perforations 690 visible along a top portion of the support tube 620). FIG. 6A is a perspective view illustration of the sheath 600 and FIG. 6B is an enlarged perspective view illustration of the introducer 610 of the sheath 600 showing the introducer 610 in a deflected position. The support tube 620 allows the cannula 300 to pass though the sheath 600 and into the introducer 610. In some embodiments, the sheath 600 can be separated from the cannula 300 (internal, not shown) by breaking the perforations 690 (shown as direction arrows 691) along the support tube 620. Because the perforations 690 intersect the cuts 612 in the introducer 610 forming the segments 611, the entire body of the introducer 600 can be split by the separating along perforations 690. With the perforations 690 broken, the sheath 600 can be removed from the cannula (not shown).

In an alternate embodiment, the sheath 600 has a longitudinal cut or split along the length of the sheath (e.g., along the location of perforations 690). In this alternate embodiment, the sheath 100 is constructed from a material sufficiently pliable to enable the sheath 600 to be removed from a cannula 300 by separating the sheath 600 along the split enough to pass the shaft 320 of the cannula 300 through the split.

Figure 7A:
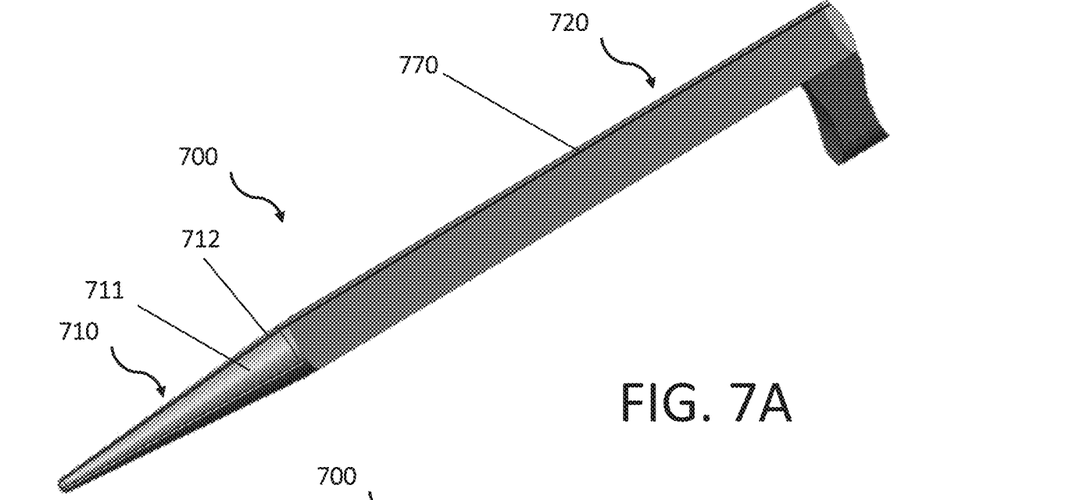
FIG. 7A-7C are illustrations of a sheath including a hinged body.
Figure 7B:
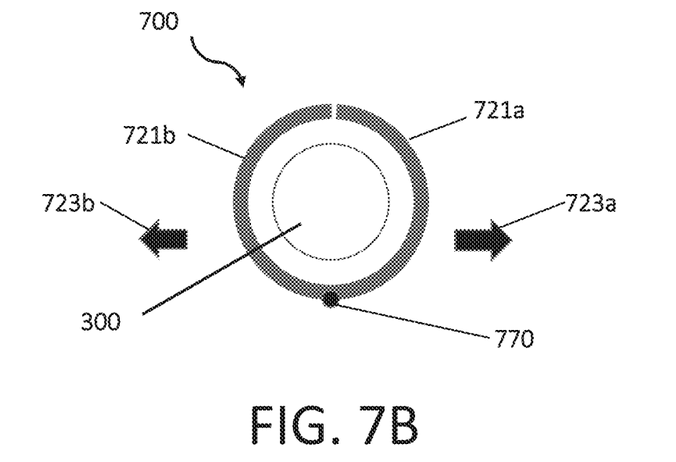
Figure 7C:
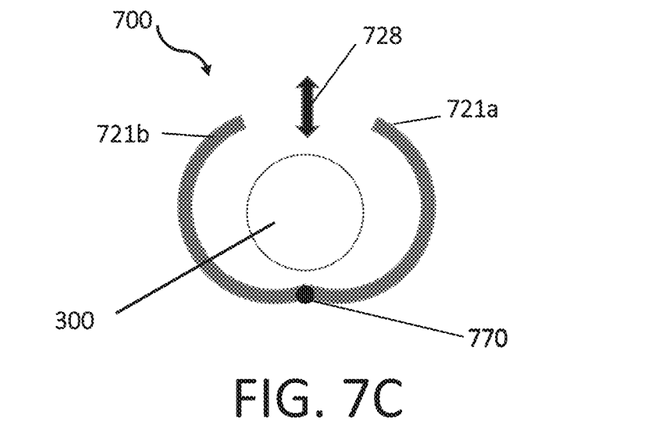

While the sheath 100 has been described as having a one-part construction, in some embodiments the sheath 100 includes two or more parts coupled together to form the sheath 100. In certain embodiments, the sheath has a two-part clamshell/hinged design enabling separation of the sheath 100 about a hinge. FIG. 7A-7C are illustrations of a sheath 700 including a hinged support tube 720 having a hinge 770 running longitudinally along the support 720. FIG. 7A is a perspective view illustration of the sheath 700 and FIGS. 7B and 7C are cross-section views of the sheath 700 showing the cannula 300 in the hinged support tube 720. FIG. 7B shows a top half 721a of the sheath 700 is, for example, hinged to a bottom half 721b of the sheath 700 by a hinge 770 that extends along the length of the sheath 700. The hinge 770 intersects the cuts 712 in the introducer 711 forming the segments 711, thereby enabling the top half 721a and bottom half 721b of the body of the sheath 700 to rotate about the hinge 700. Separating the top half 721a from the bottom half 721b (as indicated by arrows 723a,b) enables the removal or insertion (as indicated by arrows 728) of the cannula 300 to the sheath 700.

While the sheath 100 has been described as a disposable sheath, in some embodiments the sheath is reusable.

While the sheath 100 has been shown as including a retention clasp 130 at the proximal end of the support channel 120, the retention clasp 130 can alternatively be integrated with the support channel 120 between the introducer 110 and the proximal end of the sheath 100. In some embodiments, the retention clasp 130 is a strap or elastic member placed across the cannula 300 after the cannula is placed in the support channel 120. While the sheath 100 has been described as having a retention clasp 130, the sheath could alternatively include no such retention clasp.

While the introducer 110 of the sheath 100 has been shown as having triangular segments 211, different shapes can alternatively be used. For example, the segments may be rectangular with overlapping edges 213 in the relaxed state.

In some embodiments, the segments 211 of the introducer 100 are constructed from a pliable material. In some embodiments, the cuts 212 between the segments 211 are filled with a mesh or flexible material. In some embodiments, the segments 211 are removeably coupled prior to use and are separated (e.g., along cuts 212) by the distal tip 310 of the cannula 300.

While the introducer 110 and the support channel 120 have been shown as a single-piece, in some embodiments, the introducer 110 and support channel 120 are separate parts joined together to form the sheath 100.

While the pull-tab 140 has been shown as being located at the most proximal point of the sheath, the pull-tab 140 can alternatively extend from a portion of the proximal end of the sheath 100 that is distally spaced from the most proximal end surface of the sheath.

While the pull-tab 140 has been described as being positioned adjacent the vagina of a patient as the cannula 300 is being inserted into the patient, in certain embodiments, the sheath may have a length such that the proximal end of the sheath from which the pull-tab 140 extends, may be located outside of the patient during the insertion procedure.

While the sheath 100 has been described as having a pull-tab 140, the sheath could alternatively include no such pull-tab.

While the segments 211 of the introducer 110 have been described as having a normally closed configuration, the segments 211 could alternatively have a normally open position. In the normally open configuration, the segments 211 of the introducer 110 may be closed by a user's hand, for example, immediately prior to insertion of the introducer 110. In some instances, the biased-open segments 311 at least partially dilate the opening prior to insertion of the cannula 300 by removing the force holding the biased-open segments 311 in a closed position.

Referring now to FIGS. 1-3E, some examples of the present design use the sheath 100 as a dilator that is expandable after insertion. Once inserted into a patient, there could be a ratchet or tab design that allows manual splitting to expand the sheath 100 within the cervix. FIGS. 8A-8E are illustrations of a sheath 800 having a dual-sheath design. The sheath 800 enables a user to manually deflect the segments 811 of the introducer 810 prior to the introduction of the cannula 300.

Figures 8A, 8B:
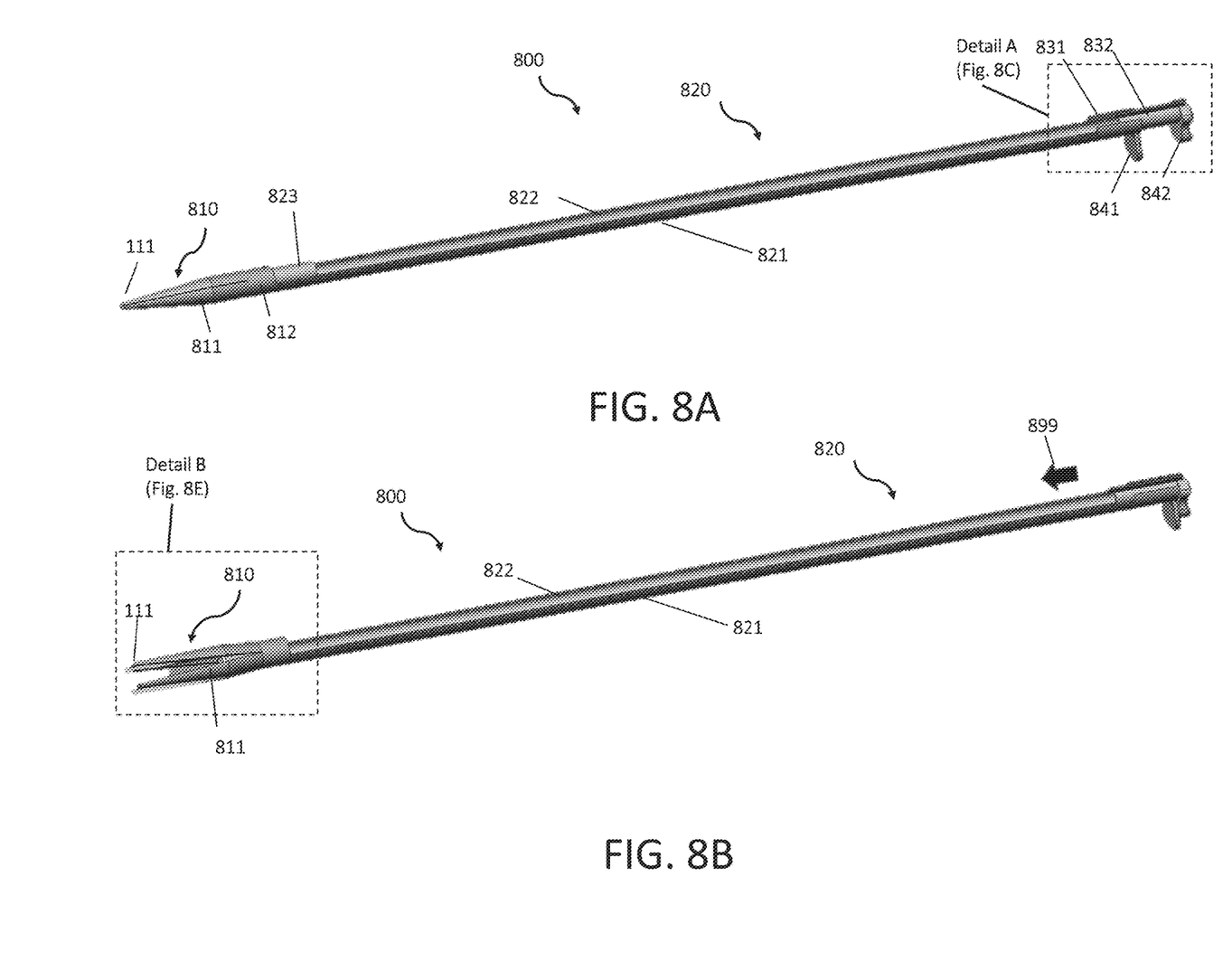
FIGS. 8A-8E are illustrations of a sheath having a dual-sleeve design.

FIG. 8A shows a sheath 800 including an outer sleeve 821, an inner sleeve 822, and an introducer 810. The outer sleeve 821 includes an outer pull-tab 841 at the proximal end of the outer sleeve 821, and the inner sleeve 822 includes an inner pull-tab 842 at the proximal end of the inner sleeve 822. The inner sleeve 822 includes an inner ring 823 positioned to be inserted into an outer ring 812 of the introducer 810. The inner sleeve 822 is positioned to align with the outer sleeve 821 and slideably coupled, such that translation of the inner sleeve 821 towards the introducer 811 (arrow 899 of FIG. 8B) engages the inner ring 823 with the segments 811 of the introducer. The inner ring 832 is sized to accept the distal tip 310 of the cannula 300. FIG. 8B shows the inner sleeve 822 translated towards the introducer 810. As shown, in more detail in FIG. 8E, the segments 811 of the introducer 810 are deflected outward by the introducer 810 of the inner ring 823 into the introducer 810.

Figure 8C:
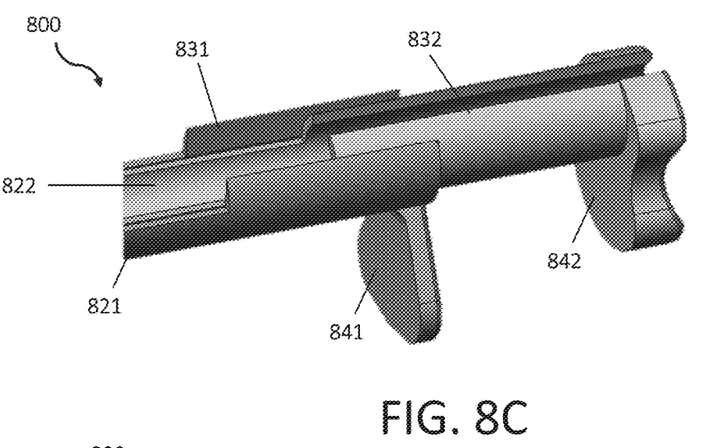
Figure 8D:
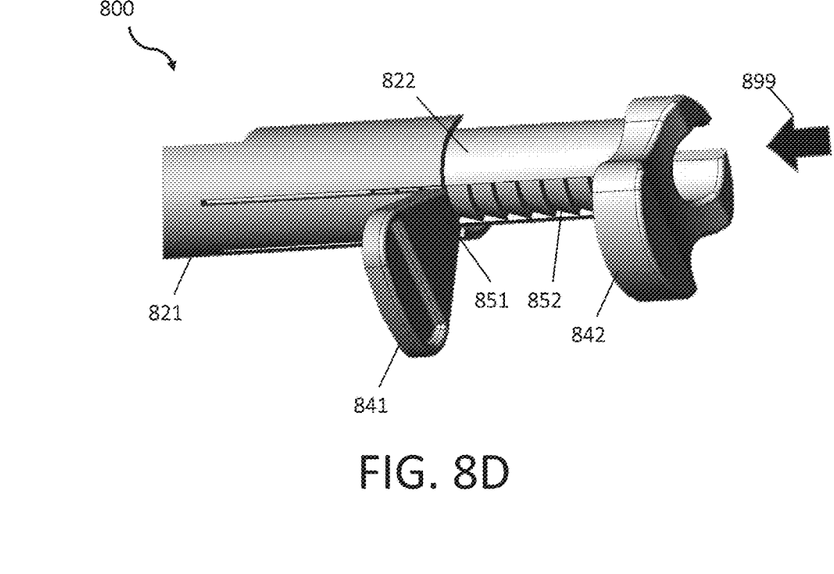
Figure 8E:
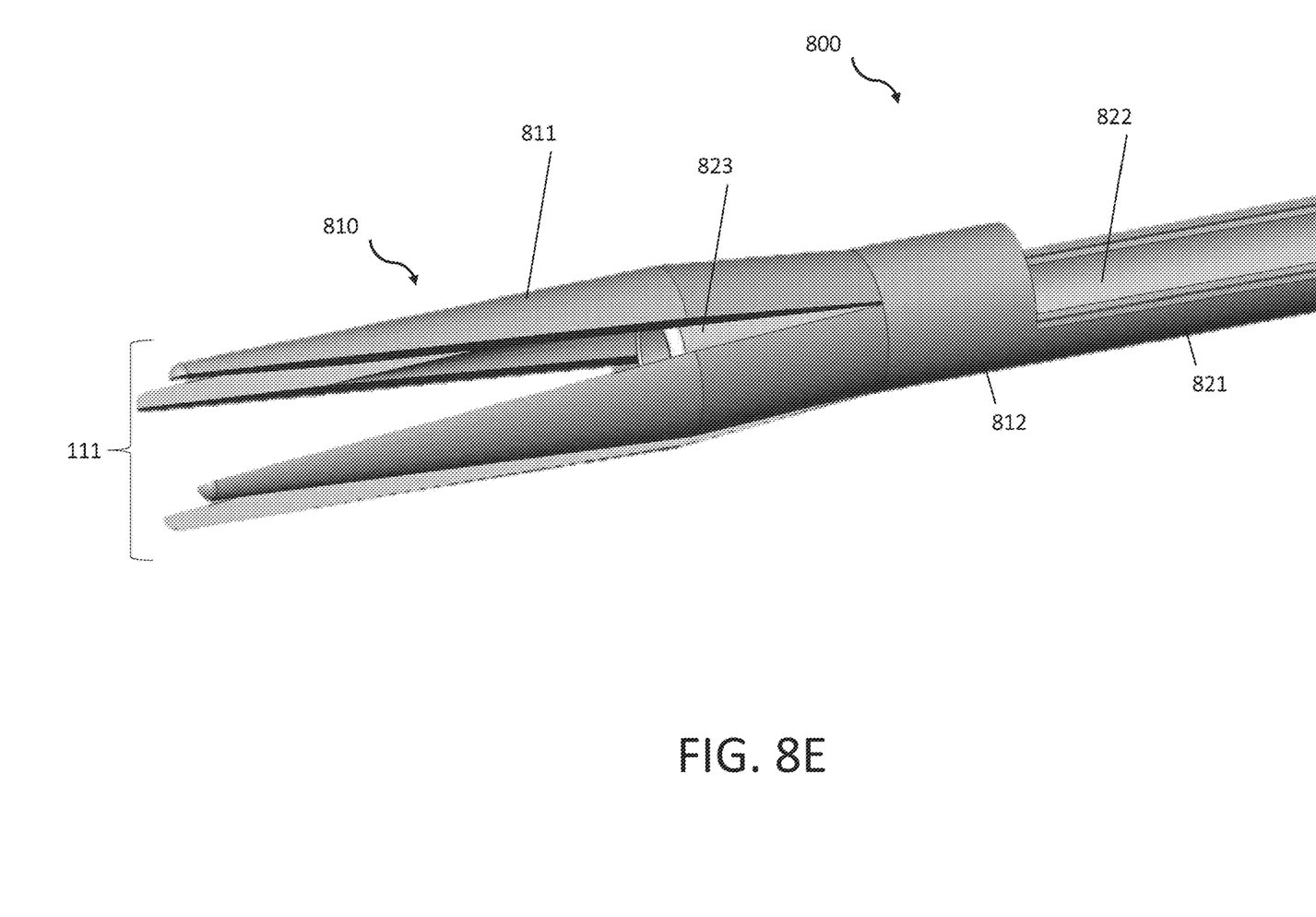
Figure 9:
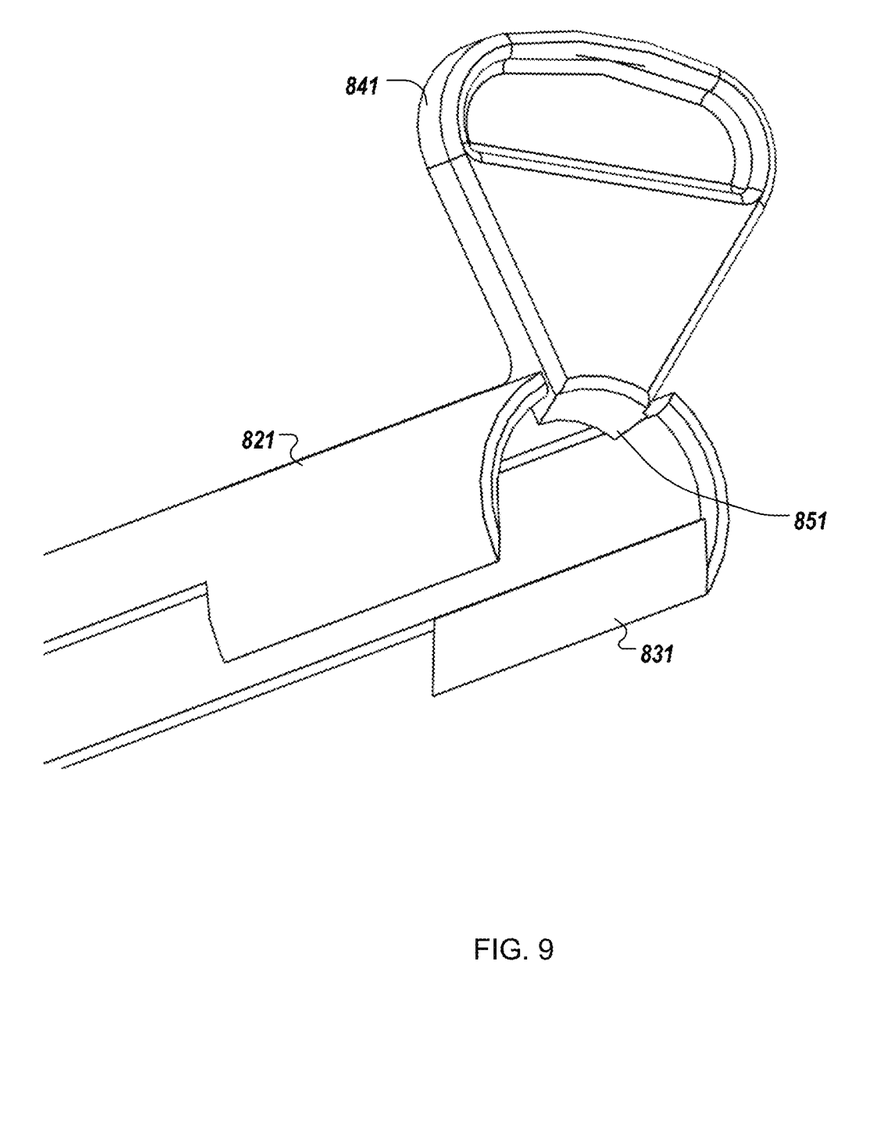
FIG. 9 is an interior, perspective view of a proximal end of an outer sleeve of the sheath of FIGS. 8A-8E.

FIG. 8C shows the proximal end of the sheath 800. The outer sleeve 821 includes a retention feature 831 removeably securing the inner sleeve 832 in a slidable configuration with the outer sleeve 821. The inner sleeve 822 includes a clasp 832 for removeably securing the shaft 310 of the cannula 300 in the inner sleeve. FIG. 8D shows the underside of the proximal end of the sheath 800. The inner sleeve 822 includes ratchet features 852 positioned to engage with a pawl 851 on the outer sleeve 821, also shown in FIG. 9. In operation, a user grasps the pull-tabs 841, 842 and applies a force to squeeze the pull-tabs 841, 842 together, thereby translating the inner sleeve 822 towards the outer sleeve 821 (as indicated by arrow 899). Distal translation of the inner sleeve 822 engages the pawl 851 with the ratchet features 852, thereby preventing reverse (e.g., proximal) motion of the inner sleeve 822 when the user removes the force. As shown in FIG. 8E, translation of the inner sleeve 822 towards the introducer 810 engages the inner ring 832 with the segments 811 of the introducer 810, thereby deflecting the segments 811 in an outward direction.

In operation, the introducer 810 is inserted into the cavity of a patient and the user translates the inner sleeve 822 towards the introducer 810, thereby deflecting the segments 811 and dilating the cavity of the patient. The ratchet features 852 maintain the deflection of the segments 811 by securing the position of the inner sleeve 822. A cannula 300 is inserted though the inner ring 832, through the introducer 810, and into the cavity of the patient. The clasp 832 secures the cannula 300 to the sheath 800. To remove the sheath 800 from the patient, in some instances, the cannula 300 is detached from the clasp 832 and the sheath 800 is removed from the patient while the cannula 300 remains inside. In some instances, the sheath 800 and cannula 300 are removed together, for example by the user pulling on the outer pull-tab 841 with the cannula 300 secured by the clash 832. In some instances, the cannula 300 is detached from the clasp 832 and removed from the patient, prior to subsequent removal of the sheath 800 from the patient.

What is claimed is:

1. A sheath for facilitating insertion of a cannula of an endoscope into an internal space of a patient, the sheath comprising:
   an outer sleeve including a pawl;
   an inner sleeve including one or more ratchet features configured to engage the pawl, the inner sleeve slidably disposed in the outer sleeve and adapted to receive a shaft of the cannula; and
   an introducer positioned at a distal end of the outer sleeve, the introducer having a tip end and an open end at a distal end of the introducer, the open end being sized and shaped to accept a tip of the cannula, the tip end adapted to be deflected in an outward direction.

2. The sheath of claim 1, wherein the tip end of the introducer is adapted to be deflected in the outward direction by the inner sleeve when a distal end of the inner sleeve is inserted into the introducer.

3. The sheath of claim 1, wherein the introducer is biased in a normally closed position.

4. The sheath of claim 1, wherein the introducer is biased in a normally deflected position, and the tip end adapted to be deflected inwardly prior to insertion of the sheath.

5. The sheath of claim 1, wherein the tip end is adapted to be deflected in the outward direction by the tip of the cannula when the tip of the cannula is inserted into the introducer.

6. The sheath of claim 1, further including an inner pull-tab extending from the inner sleeve, the inner pull-tab providing a finger hold for a user to grasp the sheath.

7. The sheath of claim 1, further including an outer pull-tab extending from the outer sleeve, the outer pull-tab providing a finger hold for a user to grasp the sheath.

8. The sheath of claim 1, wherein the inner sleeve includes a retention feature adapted to removeably secure the inner sleeve in a slidable configuration with the outer sleeve.

9. The sheath of claim 1, wherein the inner sleeve includes a clasp adapted to removeably secure the shaft of the cannula in the inner sleeve.

10. The sheath of claim 1, wherein the inner sleeve has an open, semi-cylindrical body that defines an inner channel, the inner channel being exposed to an exterior.

11. The sheath of claim 1, wherein the outer sleeve has an open, semi-cylindrical body that defines an outer channel, the outer channel adapted to slideably receive the inner sleeve.

12. The sheath of claim 1, wherein the introducer includes:
   an outer ring that at least partially defines the open end; and
   a plurality of tapered segments extending from the outer ring to the tip end, the plurality of tapered segments having a normally closed position defining a conical exterior shape of the introducer, the plurality of tapered segments adapted to be separated in a radial direction by the tip of the cannula when the tip of the cannula is passed through the introducer.

13. The sheath of claim 12, wherein each of the plurality of tapered segments comprises a conic segment.

14. The sheath of claim 12, wherein each of the plurality of tapered segments defines outside edges, the outsides edges of each of the plurality of tapered segments positioned adjacent to the outside edge of an adjacent tapered segment in the normally closed position, and the outsides edges of each of the plurality of tapered segments adapted to be separated by the tip of the cannula when the tip of the cannula is passed through the introducer.

15. The sheath of claim 12, wherein the inner sleeve includes an inner ring adapted to be inserted into the outer ring.

16. The sheath of claim 15, wherein the plurality of tapered segments are adapted to be separated in a radial direction by the inner ring when the inner ring is engaged with the plurality of tapered segments.

* * * * *